United States Patent [19]

Yano et al.

[11] Patent Number: 4,834,550

[45] Date of Patent: May 30, 1989

[54] APPARATUS FOR TESTING HEAT-INSULATING TUBULAR MEMBER

[75] Inventors: Mitsuru Yano, Okagaki; Hajime Hiramatsu, Hiroshima; Hiroshi Takaki, Yasugi, all of Japan

[73] Assignees: Hitachi Metals, Ltd., Tokyo; Shoei Manufacturing Co., Ltd., Osaka; San-In Sanso Co., Ltd., Tottori, all of Japan

[21] Appl. No.: 81,757

[22] Filed: Aug. 5, 1987

[30] Foreign Application Priority Data

Aug. 6, 1986 [JP] Japan ................................ 61-185951
Aug. 6, 1986 [JP] Japan ................................ 61-185952
Aug. 6, 1986 [JP] Japan ................................ 61-185953

[51] Int. Cl.⁴ .......................... G01N 3/60; G01N 17/00
[52] U.S. Cl. ...................... 374/57; 73/118.1; 73/865.9
[58] Field of Search .............. 73/119 R, 118.1, 117.1, 73/865.9, 865.6; 374/45, 57

[56] References Cited

U.S. PATENT DOCUMENTS

| | | | |
|---|---|---|---|
| 3,441,381 | 4/1969 | Keith et al. | 73/118.1 |
| 3,478,580 | 11/1969 | Siemietkowski et al. | 73/865.9 |
| 3,479,882 | 11/1969 | Pospisil et al. | 73/865.9 |
| 3,534,597 | 10/1970 | Webb | 374/57 |
| 3,667,914 | 6/1972 | Penquite | 73/118.1 |
| 3,969,932 | 7/1976 | Rieger et al. | 73/118.1 |
| 4,510,807 | 4/1985 | Tokutake et al. | 73/865.9 |

FOREIGN PATENT DOCUMENTS

| | | | |
|---|---|---|---|
| 1447993 | 7/1969 | Fed. Rep. of Germany | 73/119 R |
| 0180388 | 3/1966 | U.S.S.R. | 374/45 |
| 0724788 | 3/1980 | U.S.S.R. | 73/865.9 |
| 0800774 | 1/1981 | U.S.S.R. | 73/119 R |
| 1111050 | 8/1984 | U.S.S.R. | 73/119 R |

OTHER PUBLICATIONS

Drummond, "Simulated Rocket Engine Dynamic Force-Pressure Measurment System"; Proceedings of the 15th Int. ISA AeroSpace Insdrum. Symposium, Las Vegas, Nev., May 1969, pp. 10-17.

Primary Examiner—William A. Cuchlinski, Jr.
Assistant Examiner—Thomas B. Will
Attorney, Agent, or Firm—Finnegan, Henderson, Farabow, Garrett & Dunner

[57] ABSTRACT

An apparatus for testing a heat-insulating tubular member having at least one tubular portion comprising a combustion chamber connected to the tubular portion, a burner mounted in each combustion chamber, and an air line and a fuel supply line both connected to the burner. It may further comprise an air line for increasing exhaust gas pressure which opens on the inner wall of the combustion chamber near the burner.

10 Claims, 5 Drawing Sheets

APPARATUS FOR TESTING HEAT-INSULATING TUBULAR MEMBER

BACKGROUND OF THE INVENTION

The present invention relates to an apparatus for testing the heat resistance, heat insulation, etc. of heat-insulating tubular members such as exhaust equipment for internal engines of automobiles. In the development of new engines, exhaust equipment attached thereto is also evaluated. For instance, the evaluation of manifolds is usually carried out by mounting them to completed engines. Accordingly, only after the completion of engines, manifolds can be evaluated, resulting in an extremely elongated period of engine development.

OBJECT AND SUMMARY OF THE INVENTION

An object of the present invention is, therefore, to solve the above problems, thereby providing an apparatus for testing the heat resistance and heat insulation of heat-insulating tubular members without awaiting the completion of engines. The apparatus for testing a heat-insulating tubular member having at least one tubular portion according to the present invention comprises a combustion chamber connected to the tubular portion, a burner mounted in the combustion chamber, and an air line and a fuel supply line both connected to the burner. The combustion chamber may have another air line for increasing exhaust gas pressure opening on the wall thereof near the burner. An air source may be common or different to the air line for increasing exhaust gas pressure and the above air line for fuel combustion.

DETAILED DESCRIPTION OF THE INVENTION

Figure 1:
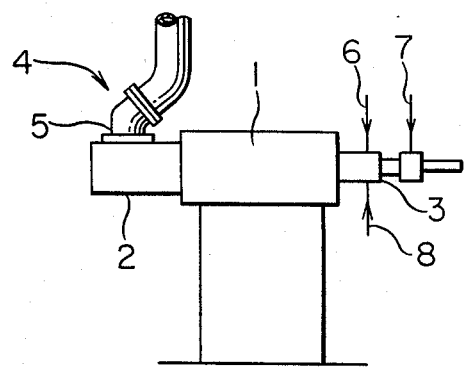
FIG. 1 is a schematic side view showing the test apparatus according to one embodiment of the present invention.

The apparatus for testing heat-insulating tubular members according to the present invention will be explained in detail referring to the drawings attached hereto.

Figure 2:
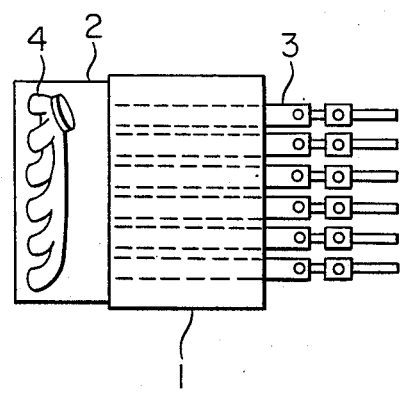
FIG. 2 is a plan view of the apparatus of FIG. 1.

FIG. 1 is a side view showing an apparatus for testing heat-insulating tubular members according to one embodiment of the present invention, and FIG. 2 is a plan view of that apparatus. The test apparatus comprises a combustor 1, an intermediate member 2 and a connecting member 3, and the intermediate member 2 is connected with a tubular portion 5 of a manifold 4 as a heat-insulating tubular member. And the connecting member 3 is connected with a first air line 6, a second air line 7 and a fuel gas supply line 8.

Figure 3:
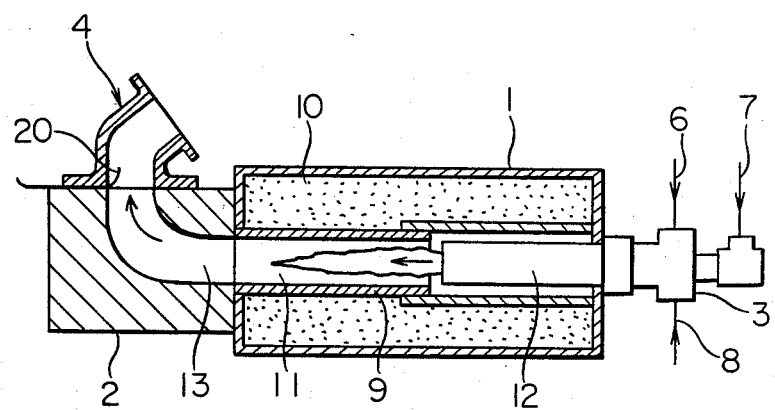
FIG. 3 is an enlarged, partially cross-sectional view showing an important portion of the test apparatus according to one embodiment of the present invention.

FIG. 3 is an enlarged, partially cross-sectional view showing an important portion of the test apparatus of FIG. 1. The combustor 1 is composed of an inner wall 9 and a heat-insulating portion 10 surrounding the inner wall 9 and made of heat-insulating materials like a ceramic tube, etc. The inner wall 9 constitutes a combustion chamber 11 which contains a burner 12 on the opposite side to the intermediate member 2. The intermediate member 2 is formed with an exhaust gas path 13 whose outlet is connected to the opening of the tubular portion of the manifold 4. The other end of the manifold is provided with a tube for withdrawing exhaust gas.

Figure 4:
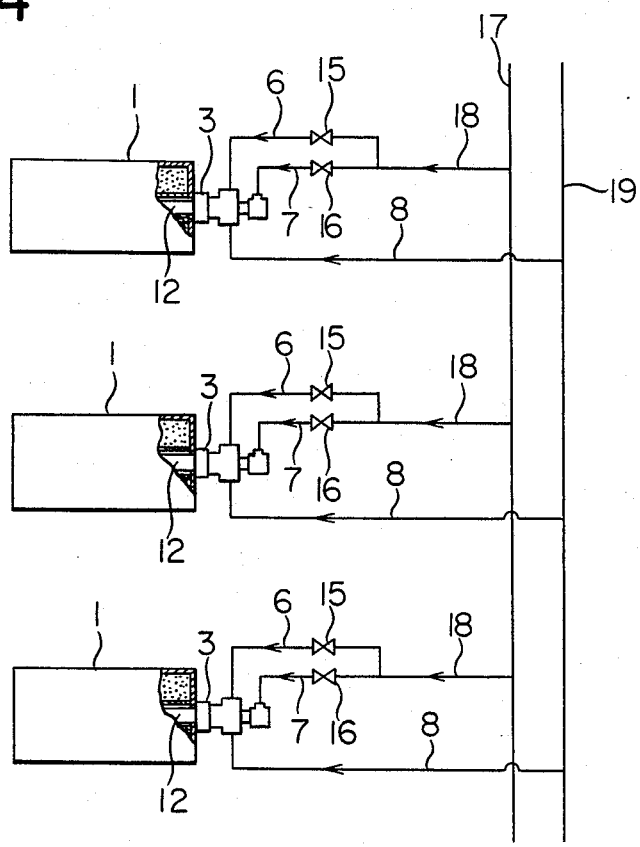
FIG. 4 is a schematic view showing a system for supplying air and a fuel gas to the test apparatus of FIG. 3.

FIG. 4 shows a system for supplying air and a fuel gas to the combustor of FIG. 1. In each combustor 1, the burner 12 is connected with the first air line 6, the second air line 7 and the fuel gas supply line 8 by the connecting member 3. The first air line 6 is for supplying air for the combustion of a fuel gas, and the second air line 7 is for adjusting the pressure of combustion gas and also for cooling an ultra-violet photosensor [not shown] for sensing the combustion.

Each of the first air line 6 and the second air line 7 is provided with a flow control valve 15, 16. The air line 6 and the second air line 7 are connected to branch lines 18 branching from a main line 17 connected to a blower [not shown] as an air source. And each fuel gas supply line 8 is branching from a main line 19 connected to an LPG gas tank [not shown] as a gas reservoir.

With the test apparatus having the above-mentioned structure, the manifold is tested with respect to heat resistance, heat insulation, etc. First, the manifold 4 is mounted to the intermediate member 2 with their openings aligned, and the burner 12 is supplied with air through the first air line 6 and the second air line 7 and with an LPG gas through the fuel gas supply line 8, so that combustion takes place in the combustion chamber 11 by ignition. A flame is jetted from the burner 12 into the combustion chamber 11 and an exhaust gas of high temperature flows into the manifold 4 as a heat-insulating tubular member through the exhaust gas path 13 of the intermediate member 2.

The temperature of the manifold 4 is detected by a temperature sensor 20 such as a thermocouple, etc., and the combustion by the burner 12 is controlled so that exhaust gas from the burner 12 may be the same as actual exhaust gas from engines. This control is carried out by adjusting the air flow of the first air line 6 and of the second air line 7 and gas flow of the fuel gas supply line 8.

Figure 5:
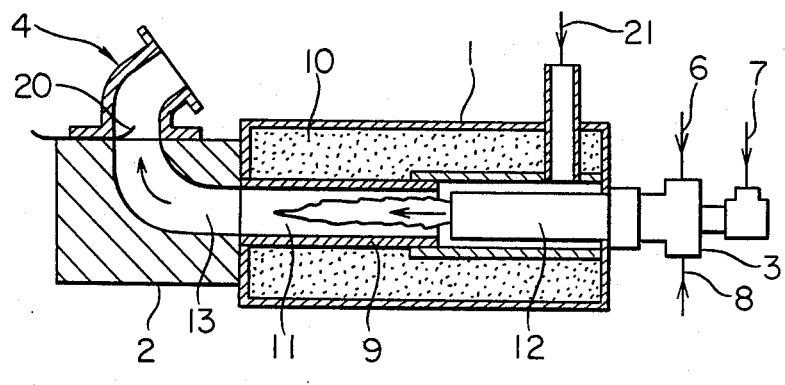
FIG. 5 is an enlarged, partially cross-sectional view showing an important portion of the test apparatus according to another embodiment of the present invention.

FIG. 5 shows a test apparatus according to another embodiment of the present invention. This test apparatus is equipped with an air line 21 for increasing exhaust gas pressure which opens into the combustion chamber 11 near the burner 12. The other parts of the apparatus are essentially the same as those in FIG. 3.

Figure 6:
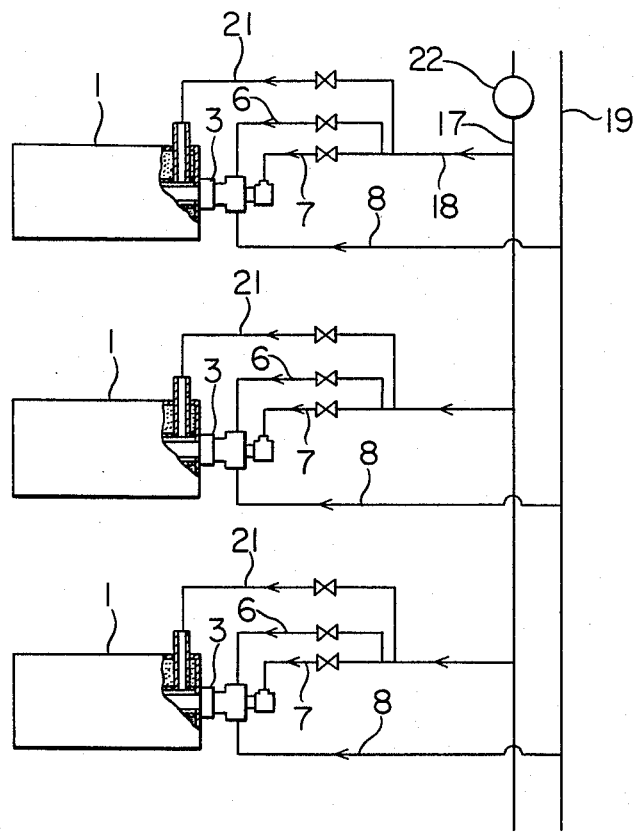
FIG. 6 is a schematic view of a system for supplying air and a fuel gas to the test apparatus of FIG. 5.

FIG. 6 shows a system for supplying air and a fuel gas to the test apparatus of FIG. 5. The air line 21 for increasing exhaust gas pressure branching from each air supply pipe 18 is communicated with the combustion chamber 11 near the burner 12, to adjust the pressure of the exhaust gas flowing from the combustion chamber 11 into the manifold 4 to actual engine exhaust gas pressure. The main line 17 is equipped with a flowmeter 22 which supplies a detection signal based on which exhaust gas pressure is adjusted. This is because exhaust gas pressure is substantially dependent upon the total flow of air supply.

Figure 7:
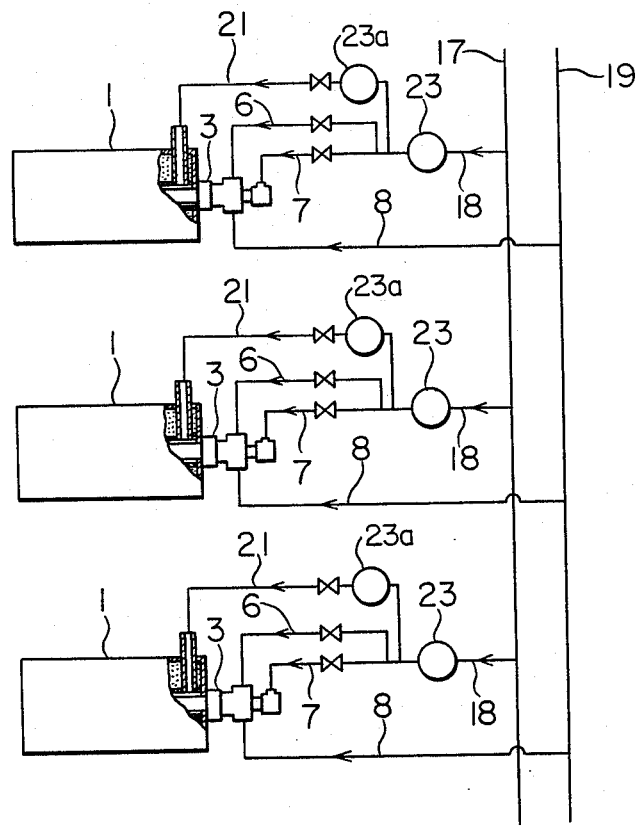
FIG. 7 is a schematic view showing a further example of a system for supplying air and a fuel gas to the test apparatus of FIG. 5.

FIG. 7 shows a further example of a system for supplying air and a fuel gas to the test apparatus of FIG. 5. In this embodiment, a flowmeter 23 is mounted to each branch tube 18. A plurality of tubular portions 5 of the manifold 4 have usually different flow resistances, so that the flowmeters 23 provided on the branch lines 18 detect the amount of exhaust gas flowing into each tubular portion 5 of the manifold 4 exactly, making it possible to carry out accurate control of the exhaust gas pressure. A further flowmeter 23a can be mounted to each air line 21, if desired.

The test method of a manifold by the apparatus shown in FIGS. 5-7 are essentially the same as by the apparatus of FIGS. 3 and 4, but the provision of the air line 21 for increasing exhaust gas pressure makes it easier to control exhaust gas pressure.

Figure 8:
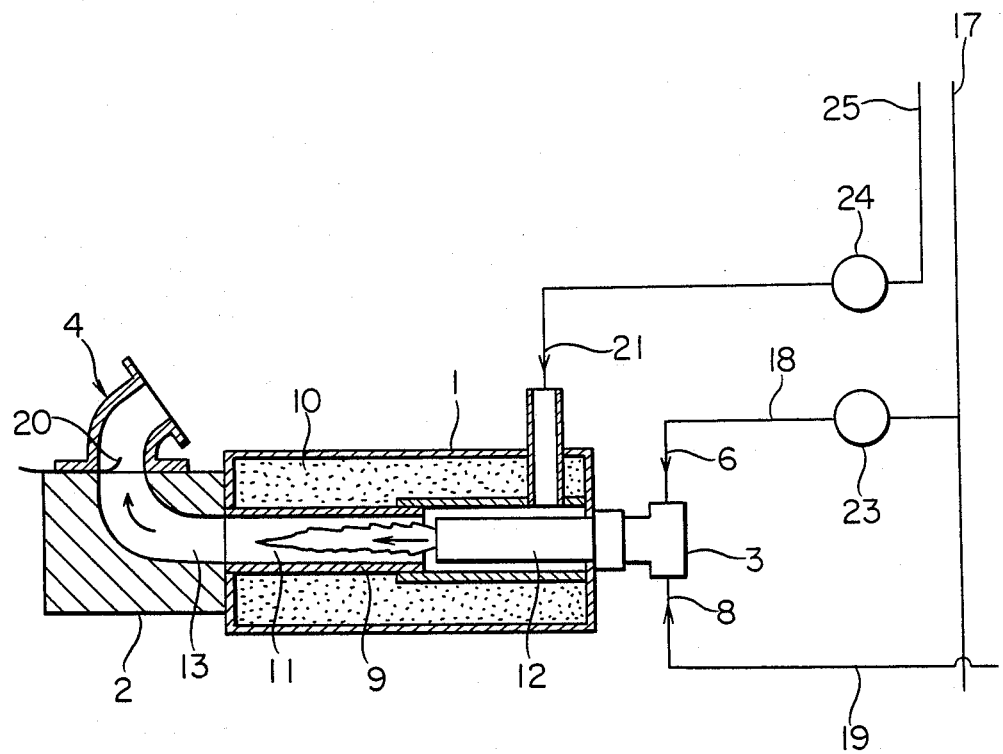
FIG. 8 is an enlarged, partially cross-sectional view showing an important portion of the test apparatus according to a further embodiment of the present invention.

FIG. 8 shows a test apparatus according to a still further embodiment of the present invention. In this apparatus, the air line 21 for increasing exhaust gas pressure is connected to a different air source [blower] from that of the main line 17, and the second air line 7 is eliminated. A separate flowmeter 24 is mounted on air line 21. With respect to other parts, it is substantially the same as in FIG. 7.

In general, exhaust resistance may vary depending on manifolds to be tested, meaning that the amount of air necessary for increasing exhaust gas pressure may largely differ for each tubular portion. However, in the apparatus of FIG. 7, the first air line 6 for supplying combustion air and the air line 21 for increasing the exhaust gas pressure are branching from the same air source [blower], so the above variation is inevitably caused by the variation of the amount of combustion air flowing through the first air line 6 sharing a common air source with the air line 21 for increasing exhaust gas pressure, resulting in the deviation of an LPG gas-air ratio from an optimum combustion mixture ratio [LPG 1:air 2]. This may make it difficult to burn a fuel gas stably. Accordingly, the optimum fuel-air mixture ratio should be kept always.

Thus, by providing a blower [not shown] for the air line 21 for increasing exhaust gas pressure independently of the first air line 6 as is shown in FIG. 8, the flow rate of air supplied through the first air line 6 can become unaffected by the variation in air flow through the air line 21 for increasing exhaust gas pressure. This makes it possible to maintain the optimum fuel gas-air ratio stably and also to adjust the pressure of the exhaust gas. Therefore, in the apparatus of FIG. 8, the second air line 7 for adjusting the exhaust gas pressure is eliminated.

The test apparatus of the present invention has been explained referring to the above embodiments, but the present invention is not restricted thereto and various modifications may be made within the scope of the present invention defined by the claims attached hereto. For instance, the burner 12 may be of any type, a fuel-air mixture type or non-mixture type gas burner or oil burner. And through the intermediate member 2 is usually like a cylinder head, it may be omitted depending upon the types of heat-insulating tubular members to be tested.

Because of the above structural features, the apparatus for testing heat-insulating tubular members according to the present invention has the following advantages:

(1) since the burner is mounted in the combustion chamber, combustion gas by the burner directly flows into the tubular portions of the heat-insulating tubular member, making it possible to carry out the test of heat resistance, heat insulation, etc. of the heat-insulating tubular member under the same conditions as actual engine exhaust gas.

(2) since it has a plurality of combustion chambers each of which is provided with a burner, it is suitable for testing a heat-insulating tubular member such as a manifold having a plurality of tubular portions.

(3) further since an air line for increasing exhaust gas pressure is connected to a combustion chamber, the exhaust gas pressure applied to the heat-insulating tubular member can be adjusted to substantially equal to pressure of actual exhaust gas. Particularly with an air line for the burner and an air line for increasing exhaust gas pressure connected to separate air sources, exhaust gas pressure can be kept stable for any heat-insulating tubular members.

What is claimed is:

1. An apparatus for testing heat-insulating members each having at least one tubular portion, comprising at least one combustion chamber connectable to said one tubular portion and having an inner wall, a burner mounted in said one combustion chamber, and an air line and a fuel supply line both connected to said burner, the apparatus further comprising a second air line for increasing exhaust gas pressure which opens on the inner wall of said combustion chamber near said burner.

2. The apparatus for testing heat-insulating tubular members according to claim 1 wherein said air line comprises a main tube and a branch tube connecting said main tube to said burner, and wherein said second air line for increasing exhaust gas pressure is connected to said main tube, and both of said second air line for increasing exhaust gas pressure and said branch tube of said air line are equipped with flowmeters.

3. The apparatus for testing heat-insulating tubular members according to claim 1, further comprising a temperature sensor locatable in the tubular portion of he heat-insulating tubular member.

4. The apparatus for testing heat-insulating tubular members according to claim 1, wherein said air line comprises a main portion and a branch portion.

5. An apparatus for testing heat-insulating tubular members each having at least one tubular portion, comprising at least one combustion chamber connectable to said one tubular portion, a burner mounted in said one combustion chamber, and an air line and a fuel supply line both connected to said burner, wherein said air line comprises a main tube and a branch tube connecting said main tube to said burner, said main tube being equipped with a flowmeter.

6. An apparatus for testing heat-insulating tubular members each having at least one tubular portion, comprising at least one combustion chamber connectable to said one tubular portion, a burner mounted in said one combustion chamber, and an air line and a fuel supply line both connected to said burner, the apparatus including a plurality of combustion chambers each with a respective burner, wherein said air line comprises a main tube and a plurality of branch tubes connecting said main tube to each burner, each of said branch tubes being equipped with a flowmeter.

7. An apparatus for testing heat-insulating tubular members each having at least one tubular portion, comprising combustion chamber connectable to said one tubular portion and having an inner wall, a burner mounted in said combustion chamber, an air line and a fuel supply line both connected to said burner and a second air line for increasing exhaust gas pressure opening on the inner wall of said combustion chamber near said burner and connected to a separate air source from that of said air line, for supplying high temperature exhaust gas to the heat-insulating tubular members at a desired pressure.

8. The apparatus for testing heat-insulating tubular members according to claim 7, wherein said air line comprises a main tube, and a branch tube for connecting said main tube to said burner, said main tube being equipped with a flowmeter.

9. The apparatus for testing heat-insulating tubular members according to claim 7 including a plurality of combustion chambers, each with a respective burner, wherein said air line comprises a main tube and a plurality of branch tubes for connecting said main tube to each burner, each of said branch tubes being equipped with a flowmeter.

10. The apparatus for testing heat-insulating tubular members according to claim 7 further comprising a temperature sensor locatable in the tubular portion of the heat-insulating tubular members.

* * * * *